United States Patent [19]

Bargiotti et al.

[11] 4,325,946
[45] Apr. 20, 1982

[54] ANTHRACYCLINE GLYCOSIDES, THEIR PREPARATION, USE AND COMPOSITIONS THEREOF

[75] Inventors: Alberto Bargiotti, Milan; Giueseppe Cassinelli, Voghera; Sergio Penco, Milan; Federico Arcamone, Nerviano; Aurelio di Marco, Milan, all of Italy

[73] Assignee: Farmitalia Carlo Erba S.p.A., Milan, Italy

[21] Appl. No.: 182,119

[22] Filed: Aug. 28, 1980

[30] Foreign Application Priority Data

Sep. 1, 1979 [GB] United Kingdom ............... 30392/79

[51] Int. Cl.$^3$ ...................... A61K 31/71; C07H 15/22; C07H 15/24
[52] U.S. Cl. ...................................... 424/180; 435/78; 536/17 A; 536/18; 536/53; 424/181
[58] Field of Search .......................... 536/18, 53, 17 A; 424/180

[56] References Cited

U.S. PATENT DOCUMENTS

| | | | |
|---|---|---|---|
| 3,803,124 | 4/1974 | Arcamone et al. | 536/17 R |
| 4,046,878 | 9/1977 | Patelli et al. | 536/17 A |
| 4,067,969 | 1/1978 | Penco et al. | 536/17 A |
| 4,112,076 | 9/1978 | Arcamone et al. | 536/17 A |
| 4,133,877 | 1/1979 | Masi et al. | 536/17 A |
| 4,191,755 | 3/1980 | Masi et al. | 536/17 A |
| 4,265,885 | 5/1981 | Bargiotti et al. | 424/180 |

*Primary Examiner*—Johnnie R. Brown

*Attorney, Agent, or Firm*—Sheldon Palmer; Peter L. Berger

[57] ABSTRACT

Anthracycline glycosides of the formula I

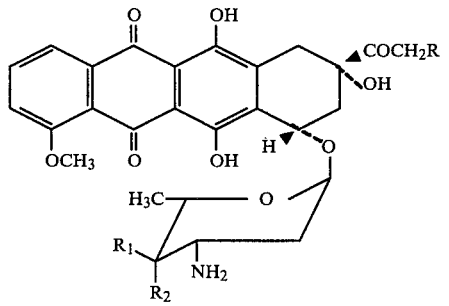

wherein R is hydrogen or hydroxy, one of $R_1$ and $R_2$ is methyl and the other of $R_1$ and $R_2$ is hydroxy, and pharmaceutically acceptable acid addition salts thereof, which are useful in treating certain mammalian tumors, are prepared by condensing daunomycinone with certain novel sugars in an inert organic solvent and in the presence of a soluble silver salt and a dehydrating agent to form the corresponding protected glycosides from which the protecting groups are removed. This gives the compounds wherein R is hydrogen. The former are converted to the corresponding hydroxyl compounds by treatment with bromine and sodium formate.

14 Claims, No Drawings

ANTHRACYCLINE GLYCOSIDES, THEIR PREPARATION, USE AND COMPOSITIONS THEREOF

CROSS REFERENCE TO RELATED APPLICATIONS

This application is related to and incorporates by reference the contents of U.S. Pat. Nos. 3,803,124; 4,112,076; and U.S. Patent Application Ser. No. 082,293, filed on Oct. 5, 1979, U.S. Pat. No. 4,265,885, all of which are owned by the unrecorded assignee hereof.

BACKGROUND OF THE INVENTION

1. Field of the Invention

The present invention relates to anthracycline antitumor glycosides, methods for their preparation, compositions containing same and the use thereof as well as certain novel intermediates used in their preparation.

2. The Prior Art

Daunorubicin (daunomycin) and doxorubicin (adramycin) are both well known anthracycline antitumor glycosides, and both their preparation and use are amply described in the prior art. Daunomycinone, the aglycone of daunorubicin, which is one of the starting materials used in the preparation of the compounds of the invention is also a well known material and is described and claimed in British Pat. No. 1,003,383, owned by the unrecorded assignee hereof.

SUMMARY OF THE INVENTION

The present invention provides, in one aspect thereof, a new class of anthracycline glycoside antibiotics of the formula I:

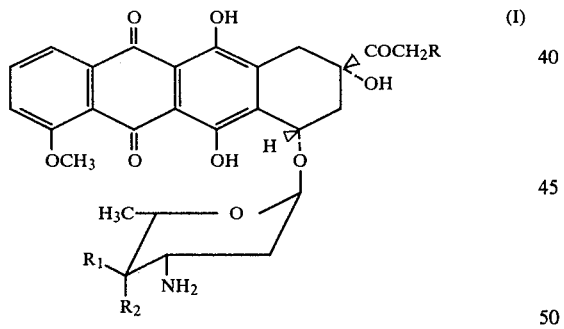

wherein R is hydrogen or hydroxy, one of $R_1$ and $R_2$ is methyl and the other of $R_1$ and $R_2$ is hydroxy, and the hydrochlorides thereof. This class of anthracycline glycosides I comprises four compounds which may be named as follows:

I-A: 4'-methyl-daunorubicin (R=H, $R_1$=CH$_3$, $R_2$=OH)

I-B: 4'-C-methyl-doxorubicin (R=$R_2$=OH, $R_1$=CH$_3$)

I-C: 4'-epi-4'-C-methyl-daunorubicin (R=H, $R_1$=OH, $R_2$=CH$_3$)

I-D: 4'-epi-4'-C-methyl-doxorubicin (R=$R_1$=OH, $R_2$=CH$_3$)

Compounds I-A and I-C are prepared by a method which is also within the scope of the invention, said method involving the use of two novel halosugars that are also part of the invention. Moreover, the process by which the halosugars are made is also within the scope of the invention.

Thus, in another aspect, the invention provides a method for the preparation of compounds I-A and I-C. According to the method, the known compound daunomycinone (the aglycone of daunorubicin) is condensed with 2,3,6-trideoxy-4-C-methyl-4-O-p-nitrobenzoyl-3-trifluoroacetamido-L-lyxo-hexopyranosyl chloride (II-A) or 2,3,6-trideoxy-4-C-methyl-4-O-p-nitrobenzoyl-L-arabino-hexopyranosyl chloride (II-B) having the formulae:

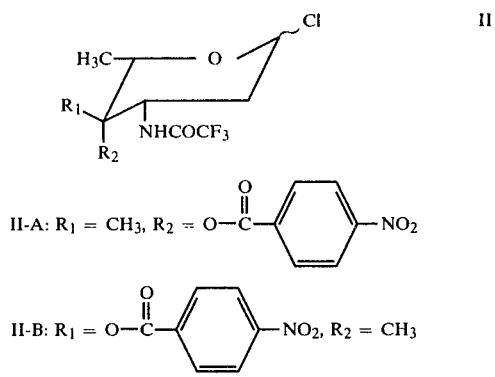

in an inert organic solvent, in the presence of a soluble silver salt as a catalyst, and a molecular sieve as a dehydrating agent to form the protected glycosides of the formula:

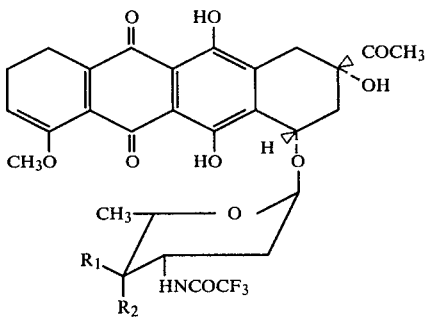

wherein $R_1$ is CH$_3$ and $R_2$ is 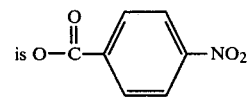

or vice versa, and removing the N-trifluoroacetyl protecting groups therefrom by mild alkaline hydrolysis. Compounds I-A and I-C may then be isolated as their hydrochlorides.

The inert organic solvent in which the condensation is carried out is preferably methylene dichloride or chloroform. The soluble silver salt is preferably silver trifluoromethanesulphonate, and the molecular sieve is preferably Merck molecular sieve. The conditions under which the condensation is carried out may be those described in U.S. Pat. No. 4,112,076, owned by the unrecorded assignee hereof.

Compounds I-B and I-D are prepared from compounds I-A and I-C respectively by a further method which is within the scope of the invention. The said further method comprises brominating the compound I-A or I-C at the 14-position to form the respective 14-bromo derivatives and hydrolysing the 14-bromoderivatives with aqueous sodium formate to give compound I-B or I-D. The bromination and hydrolysis conditions utilized in said further method are those described in U.S. Pat. No. 3,803,124 or British Pat. No. 1,217,133, both owned by the unrecorded assignee hereof.

The protected halo-sugars IIA and II-B are also novel compounds and are within the scope of the invention.

Thus, in yet another aspect, the invention provides the novel halosugars of the formula II-A and II-B above.

In a still further aspect, the invention provides a process for preparing halosugars II-A and II-B, said process proceeding through several novel intermediates which are also part of the invention. According to this aspect of the invention, and as shown below, the protected halosugars II-A and II-B are prepared respectively from the known compounds methyl 2,3,6-trideoxy-4-C-methyl-3-trifluoroacetamido-α-L-lyxo-hexopyranoside of the formula IV-A and methyl 2,3,6-trideoxy-4-C-methyl-3-trifluoroacetamido-α-L-arabino-hexopyranoside of the formula IV-B, both of which are known compounds described in U.S. Pat. Application Ser. No. 082,293, owned by the unrecorded assignee hereof.

In accordance with this process, compound IV-A or IV-B (as the case may be) is subjected to acid hydrolysis to form, respectively, compound V-A, which is 2,3,6-trideoxy-4-C-methyl-α-L-lyxo-hexopyranose or V-B, which is 2,3,6-trideoxy-4-C-methyl-α-L-arabino-hexopyranose, which by treatment with p-nitrobenzoyl chloride in methylene dichloride and triethylamine in the presence of a catalytic amount of 4-dimethylaminopyridine are transformed into the corresponding 1,4-di-O-p-nitrobenzoyl derivatives VI-A and VI-B. Finally treatment of these compounds (VI-A and VI-B) with anhydrous hydrogen chloride in anhydrous methylene dichloride gives respectively, compounds II-A and II-B. The intermediate compounds V-A, V-B, VI-A and VI-B are also part of the invention. This process, as well as the formulae of the various involved compounds is shown in the following reaction scheme:

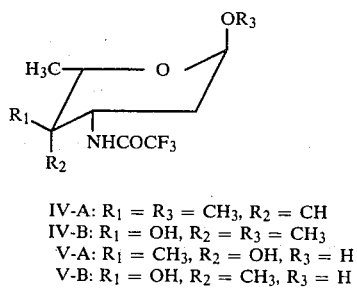

IV-A: $R_1 = R_3 = CH_3$, $R_2 = CH$
IV-B: $R_1 = OH$, $R_2 = R_3 = CH_3$
V-A: $R_1 = CH_3$, $R_2 = OH$, $R_3 = H$
V-B: $R_1 = OH$, $R_2 = CH_3$, $R_3 = H$

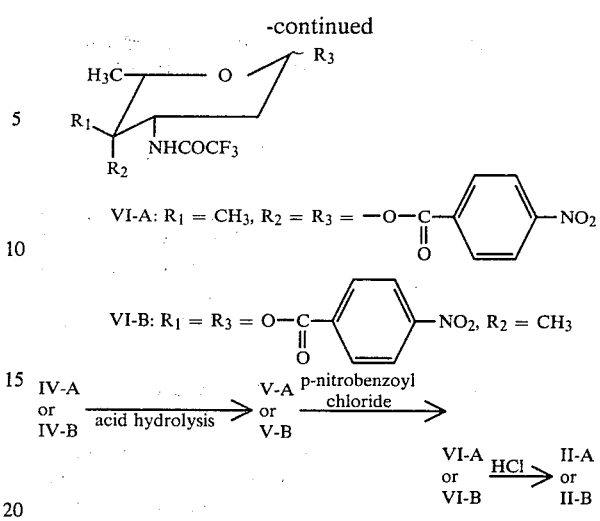

In still further aspects thereof, the invention provides pharmaceutical compositions comprising an anthracycline glycoside of the formula I or the hydrochloride thereof in combination with a therapeutically acceptable diluent or carrier therefor, as well as methods of using said compounds in treating certain mammalian tumors, for example, ascitic P-388 leukemia.

DESCRIPTION OF THE PREFERRED EMBODIMENTS

The invention is illustrated in greater detail by the following Examples:

EXAMPLE 1

4-O-p-nitrobenzoyl-2,3,6-trideoxy-4-C-methyl-3-trifuoroacetamido-L-lyxo-hexopyranosylchloride (II-A)

A solution of 1 g (3.7 mmoles) of methyl 2,3,6-trideoxy-4-C-methyl-3-trifluoroacetamido-α-L-lyxo-hexopyranoside (IV-A) in 20 ml of acetic acid and 80 ml of water was reacted at 100° C. for 2 hours. The solution was evaporated and 2,3,6-trideoxy-4-C-methyl-3-trifluoroacetamido-α-L-lyxo-hexopyranose (V-A) (0.95 g; 95%) was obtained as a white solid; m.p. 181°–182° C. $[\alpha]_D^{23°} = -127°$ (c=1.0 in methanol). The PMR spectrum (CDCl$_3$+DMSO—d$_6$) showed, inter alia, absorptions at: 1.05 (s, CH$_3$—C-4), 1.16 (d, CH$_3$-C-5), and 5.27δ(C-l-H). A solution of 0.75 g (2.9 mmoles) of compound V-A in a mixture of 10 ml of triethylamine and 20 ml of anhydrous methylene dichloride was treated under stirring with 2.20 g of p-nitrobenzoyl chloride and 0.220 g of 4-dimethylaminopyridine and then heated at 45° C. for 90 minutes. The solution was evaporated to form a residue which was dissolved in 100 ml of chloroform, washed with 10% sodium bicarbonate solution and then with water. The chloroform solution was then dried over sodium sulphate and concentrated to a residue which was chromatographed on a silica gel column. Elution with a 95:5 chloroform: acetone mixture gave 1,4-di-O-p-nitrobenzoyl-2,3,6-trideoxy-4-C-methyl-3-trifluoroacetamido-L-lyxo-hexopyranose (VI-A, 1.55 g; 95%): m.p. 168°–170° C.; $[\alpha]_D^{23°} = -35°$ (c=1 in chloroform).

A solution of 1.10 g (2.0 mmoles) of compound VI-A in 25 ml of anhydrous methylene dichloride was saturated at 0° C. with anhydrous hydrogen chloride.

The resulting precipitate of p-nitrobenzoic acid was filtered off under anhydrous conditions and the filtrate was concentrated to give 2,3,6-trideoxy-4-C-methyl-4-O-p-nitrobenzoyl-3-trifluoroacetamido-L-lyxo-hexopyranosyl chloride (II-A, 0.80 g) as a white solid suitable for the subsequent coupling reaction without further purification.

EXAMPLE 2

4-O-p-nitrobenzoyl-2,3,6-trideoxy-4-C-methyl-3-trifluoroacetamido-L-arabino-hexopyranosyl chloride (II-B)

Acid hydrolysis of methyl 2,3,6-trideoxy-4-C-methyl-3-trifluoroacetamido-α-L-arabino-hexopyranoside (IV-B, 0.80 g, 3 mmoles) as described in Example 1 gave 2,3,6-trideoxy-4-C-methyl-3-trifluoroacetamido-α-L-arabino-hexopyranose (V-B, 0.700 g, 90%) as a solid; m.p. 110°–111° C. $[\alpha]_D^{23°} = -33°$ (c=1 in methanol). The PMR spectrum (CDCl$_3$+DMSO-d$_6$) showed, inter alia, adsorptions at: 1.10 (s, CH$_3$-C-4), 1.17 (d, CH$_3$-C-5), and 5.23δ (broad s, C-1-H).

Treatment of compound V-B (0.60 g, 2.33 mmoles) with p-nitrobenzoyl chloride as described in Example 1 gave the corresponding 1,4-di-O-p-nitrobenzoyl derivative (VI-B, 1.030 g, 80%): m.p. 151° C.; $[\alpha]_D^{23°} = -21°$ (c=1.1 in chloroform).

A solution of 0.90 g (1.62 mmoles) of compound VI-B in 20 ml of anhydrous methylene dichloride was saturated at 0° C. with anhydrous hydrogen chloride. After filtering off the precipitated p-nitrobenzoic acid, the solution was evaporated to a residue to give 2,3,6-trideoxy-4-C-methyl-4-O-p-nitrobenzoyl-3-trifluoroacetamido-L-arabino-hexopyranosyl chloride (II-B, 0.650 g) as a white solid suitable for the subsequent coupling reaction without further purification.

EXAMPLE 3

4'-C-Methyl-daunorubicin (I-A)

To a solution of daunomycinone (0.900 g, 2.26 mmoles) in 90 ml of anhydrous methylene dichloride there was added 2,3,6-trideoxy-4-C-methyl-4-O-p-nitrobenzoyl-3-trifluoroacetamido-L-lyxo-hexopyranosyl chloride (II-A, 0.800 g) prepared as described in Example 1 in 15 ml of methylene dichloride and 6 g of molecular sieve (4 Å Merck). The mixture was then treated with 0.58 g of silver trifluoromethanesulphonate in 15 ml of anhydrous diethyl ether under vigorous stirring. After 1 hour at room temperature, the reaction mixture was neutralized with a saturated aqueous solution of sodium bicarbonate and the organic phase was separated off and concentrated under vacuum. Chromatographic purification of the crude residue on a silica gel column, using 95:5 chloroform: acetone as the eluent, gave 0.965 g (65%) of 4'-C-methyl-4'-O-p-nitrobenzoyl-N-trifluoroacetyl-daunorubicin, m.p. 172°–173° C.; $[\alpha]_D^{23°} = +420°$ (C=0.05 in chloroform). The PMR spectrum (CDCl$_3$) showed, inter alia, absorption at: 1.28 (d, CH$_3$-C-5'), 1.56 (s, CH$_3$-C-4'), 2.48 (s, CH$_3$CO), 4.02 (s, OCH$_3$), 5.21 (broad s, C-7-H), 5.50 (broad s, C-1'-H), 13.11 and 13.92 δ (two S, phenolic OH).

A solution of 0.8 g of the above named compound in 15 ml of acetone was treated with 45 ml of 0.1 N aqueous sodium hydroxide and stirred under nitrogen at room temperature. After 1 hour the reaction mixture was adjusted to pH 3.5 with 1 N aqueous hydrogen chloride and then extracted with chloroform to eliminate impurities. The aqueous phase, adjusted to pH 8.0, was extracted twice with chloroform. The combined chloroform extracts were dried over sodium sulphate, concentrated to a small volume and acidified to pH 4.5 with 0.25 N methanolic hydrogen chloride. Addition of excess diethyl ether gave 4'-C-methyldaunorubicin (I-A) as the hydrochloride (0.515 g, 88%), m.p. 162°–163° C. (with decomposition), $[\alpha]_D^{23°} = +320°$ (c=0.05 in methanol).

EXAMPLE 4

4'-C-Methyl-doxorubicin (I-B)

A solution of 0.450 g; 0.78 mmole of 4'-methyl-daunorubidin hydrochloride (I-A) prepared as described in Example 3, in a mixture of 6 ml of anhydrous methanol, 17.5 ml of dioxan and 0.45 ml of ethyl orthoformate was treated with 1.8 ml of a solution containing 0.95 g of bromine in 10 ml of chloroform. After 1.5 hours at 10° C. the reaction mixture was poured into a mixture of 90 ml of diethyl ether and 45 ml of petroleum ether. The resultant red precipitate, after being filtered off and washed with diethyl ether, was dissolved in a mixture of 15 ml of acetone and 15 ml of 0.25 N aqueous hydrogen bromide. After 20 hours at 30° C. the reaction mixture was treated with 0.68 g of sodium formate in 7.5 ml of water and stirred at 30° C. for 48 hours. The reaction mixture was extracted with chloroform in order to remove some lipophilic impurities. The aqueous phase, after being adjusted to pH 7.6 with aqueous sodium bicarbonate, was repeatedly extracted with chloroform until the extracts were colorless. The combined chloroform extracts were dried over sodium sulphate and evaporated to a small volume (about 20 ml) under vacuum. To the resulting red solution, adjusted to pH 3.5 with anhydrous methanolic hydrogen chloride, excess diethyl ether was added to give 4'-C-methyl doxorubicin (I-B, 0.410 g) as the hydrochloride, m.p. 185°–186° C. (with decomposition), $[\alpha]_D^{23°} = +227°$ (c=0.05 in methanol).

EXAMPLE 5

4'-Epi-4'-C-methyl-daunorubicin (I-C)

The synthesis of the title compound, starting from daunomycinone and 2,3,6-trideoxy-4-C-methyl-4-O-p-nitrobenzoyl-3-trifluoroacetamido-L-arabino hexopyranosyl chloride (II-B), prepared as described in Example 2, was carried out according to the procedure described in Example 3.

4'-Epi-4'-C-methyl-daunorubicin (I-C) was obtained as the hydrochloride in the form of red crystals, m.p. 187°–188° C. (with decomposition), $[\alpha]_D^{23°} = +285°$ (c=0.05 in methanol).

EXAMPLE 6

4'-Epi-4'-C-methyl-doxorubicin (I-D)

Compound I-C, prepared as described in Example 5, was transformed into the corresponding 14-hydroxy derivative, according to the procedure described in Example 4. 4'-Epi-4'-C-methyl-doxorubicin (I-D) was obtained as the hydrochloride in the form of red crystals, m.p. 169°–170° C. (with decomposition), $[\alpha]_D^{23°} = +250°$ (c=0.04 in methanol).

BIOLOGICAL ACTIVITY DATA

Antitumor Activity

The new compounds according to the invention were tested in HeLa cells in vitro (time of exposure to the drugs: 24 hours) and on P-388 ascitic leukemia in mice in comparison with daunorubicin (daunomycin) and doxorubicin (adriamycin).

The results of the in vitro tests are shown in Table 1.

TABLE 1

Effect on HeLa Cells Cloning Efficiency In Vitro[a]

| COMPOUND | $ID_{50}$(ng/ml) |
|---|---|
| Daunorubicin . HCl | 9 |
| 4'-C-methyl-daunorubicin . HCl (I-A) | 35 |
| 4'-epi-4'-C-methyl-daunorubicin . HCl (I-C) | 2.8 |
| Doxorubicin . HCl | 8.4 |
| 4'-C-methyl-doxorubicin . HCl (I-B) | 18 |
| 4'-epi-4'-C-methyl-doxorubicin . HCl (I-D) | 0.62 |

[a]HeLa cells were exposed to the test compounds for 24 hours, then plated. The number of colonies was evaluated 5 days later.

The in vivo data obtained in mice are reported in Table 2.

All the new compounds of the invention showed activity against P-388 leukemia at the tolerated dose which is comparable to or higher than that of the parent compounds.

TABLE 2

Activity on Ascitic P-388 Leukemia in Mice

| Compound | Dose[a] mg/Kg | T/C[b] % | Toxic[c] Deaths | LTS[d] |
|---|---|---|---|---|
| Daunorubicin . HCl | 2.9 | 175 | 0/40 | |
|  | 4.4 | 180 | 3/39 | |
| 4'-C-methyl-daunorubicin . HCl (I-A) | 10 | 150 | 0/10 | |
|  | 20 | 155 | 0/10 | |
| 4'-epi-4'-C-methyl-daunorubicin . HCl (I-C) | 0.29 | 140 | 0/10 | |
|  | 0.44 | 163 | 0/10 | |
|  | 0.66 | 158 | 1/20 | |
| Doxorubicin . HCl | 6.6 | 193 | 0/30 | 2/30 |
|  | 10 | 227 | 1/28 | 5/28 |
| 4'-C-methyl-doxorubicin . HCl (I-B) | 6 | 186 | 0/10 | |
|  | 7.7 | 172 | 0/10 | |
|  | 10 | 233 | 2/20 | 3/20 |
| 4'-epi-4'-C-methyl-doxorubbicin . HCl (I-D) | 1 | 150 | 0/10 | |
|  | 2 | 156 | 0/10 | |

[a]Mice were treated i.p. on day 1 after tumor cell inoculation.
[b]Median survival time of treated mice/median survival time of control mice × 100.
[c]Evaluated on the basis of macroscopic autoptic findings.
[d]Long-time survival.

Variations and modifications can, of course, be made without departing from the spirit and scope of the invention.

Having thus described our invention what we desire to secure by Letters Patent and hereby claim is:

1. An anthracycline glycoside of the formula:

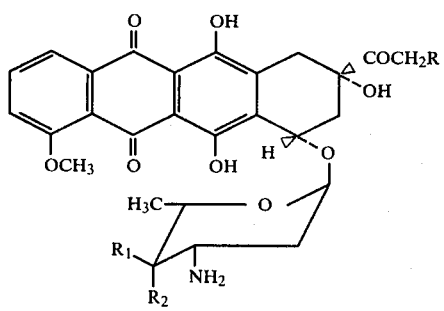

I wherein R is hydrogen or hydroxy, one of $R_1$ and $R_2$ is methyl and the other of $R_1$ and $R_2$ is hydroxy, and pharmaceutically acceptable acid addition salts thereof.

2. An anthracycline glycoside according to claim 1, which is 4'-C-methyl-daunorubicin.

3. An anthracycline glycoside according to claim 1, which is 4'-C-methyl-doxorubicin.

4. An anthracycline glycoside according to claim 1, which is 4'-epi-4'-C-methyl-daunorubicin.

5. An anthracycline glycoside according to claim 1, which is 4'-epi-4'-C-methyl-doxorubicin.

6. A sugar of the formula:

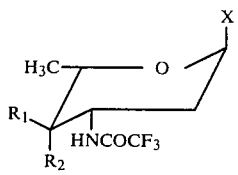

wherein X is hydroxyl, chloro or p-nitrobenzoyl, $R_1$ is methyl, or p-nitrobenzoyl and $R_2$ is methyl, or p-nitrobenzoyl, wherein one of $R_1$ and $R_2$ is methyl and the other is P-nitrobenzoyl.

7. A sugar according to claim 6 wherein X is chloro, $R_1$ is methyl and $R_2$ is p-nitrobenzoyl.

8. A sugar according to claim 6 wherein X is chloro, $R_1$ is p-nitrobenzoyl and $R_2$ is methyl.

9. A sugar according to claim 6 wherein X is p-nitrobenzoyl, $R_1$ is methyl and $R_2$ is p-nitrobenzoyl.

10. A sugar according to claim 6 wherein X is p-nitrobenzoyl, $R_1$ is p-nitrobenzoyl and $R_2$ is methyl.

11. A process for preparing the sugars according to claim 6 wherein X is chloro, one of $R_1$ and $R_2$ is methyl and the other is p-nitrobenzoyl, said process comprising separately subjecting 2,3,6-trideoxy-4-C-methyl-α-L-lyxo-hexopyranose(IV-A) and 2,3,6-trideoxy-4-C-methyl-α-L-arabinohexopyranose (IV-B) to acid hydrolysis to form respectively, sugars wherein X is hydroxy, one of $R_1$ and $R_2$ is methyl and the other is hydroxy, reacting each said sugar with p-nitrobenzoyl chloride to form the sugars wherein X is p-nitrobenzoyl, one of $R_1$ and $R_2$ is methyl and the other is p-nitrobenzoyl, and separately subjecting each said sugar to treatment with anhydrous hydrogen chloride to form said sugars wherein X is chloro, one of $R_1$ and $R_2$ is methyl and the other is p-nitrobenzoyl.

12. A process according to claim 11 wherein the acid hydrolysis is effected with acetic acid at about 100° C. for about 2 hours, the reaction with p-nitrobenzoyl chloride is effected in the presence of triethylamine and a catalytic amount of 4-dimethylamino pyridine at about 45° C. for about 1.5 hours and the treatment with anhydrous hydrogen chloride is effected at about 0° C.

13. An antitumor pharmaceutical composition, for a transplanted tumor, comprising a therapeutically effective amount of an anthracycline glycoside as claimed in claim 1 in combination with an inert carrier therefor.

14. A method of inhibiting the growth of transplanted P 388 leukemia comprising intraperitoneally administering to a host afflicted therewith, a therapeutically effective amount of an anthracycline glycoside as claimed in claim 1.

* * * * *

UNITED STATES PATENT AND TRADEMARK OFFICE
CERTIFICATE OF CORRECTION

PATENT NO. : 4,325,946
DATED : April 20, 1982
INVENTOR(S) : Alberto Bargiotti et al It is certified that error appears in the above-identified patent and that said Letters Patent are hereby corrected as shown below:

Column 5, line 60: "two S" should read --two s--.

Column 6, line 13: "daunorubidin" should read --daunorubicin--.

Signed and Sealed this

Twenty-first Day of September 1982

[SEAL]

Attest:

Attesting Officer

GERALD J. MOSSINGHOFF
Commissioner of Patents and Trademarks